United States Patent [19]

Cilento et al.

[11] 4,427,737

[45] Jan. 24, 1984

[54] MICROPOROUS ADHESIVE TAPE

[75] Inventors: Rudolfo D. Cilento, North Brunswick; Charles Riffkin, Cranbury; Anthony L. LaVia, East Brunswick, all of N.J.

[73] Assignee: E. R. Squibb & Sons, Inc., Princeton, N.J.

[21] Appl. No.: 256,279

[22] Filed: Apr. 23, 1981

[51] Int. Cl.$^3$ .......................... B32B 27/08; C09J 7/02
[52] U.S. Cl. .................. 428/315.7; 128/156; 428/317.3; 428/317.5; 428/317.7; 428/332; 428/339; 428/343; 428/355; 428/913
[58] Field of Search ............... 428/355, 343, 219, 332, 428/339, 315.7, 317.3, 317.5, 317.7; 128/156

[56] References Cited

U.S. PATENT DOCUMENTS

| 3,121,021 | 2/1964 | Copeland | 428/219 |
| 3,339,546 | 9/1967 | Chen | 128/156 |
| 3,645,835 | 2/1972 | Hodgson | 428/355 X |
| 3,972,328 | 8/1976 | Chen | 128/156 |

Primary Examiner—Thomas J. Herbert, Jr.
Attorney, Agent, or Firm—Lawrence S. Levinson; Stephen B. Davis

[57] ABSTRACT

A breathable tape comprising a porous backing layer and a microporous adhesive layer. The adhesive layer includes a rubbery elastomer, one or more water soluble or swellable hydrocolloids, and other optional substances and has a porosity of from about 1 to about 100 cc/sec/in$^2$.

12 Claims, 2 Drawing Figures

MICROPOROUS ADHESIVE TAPE

BACKGROUND OF THE INVENTION

Copeland in U.S. Pat. No. 3,121,021 describes a translucent breathable surgical adhesive tape. The tape is formed of a backing layer of porous, non-woven rayon fabric and a layer of microporous acrylic pressure-sensitive adhesive.

Chen in U.S. Pat. No. 3,972,328 describes a three layer bandage. The adhesive layer of the bandage includes a pressure sensitive rubbery elastomer having dispersed therein one or more water soluble or swellable hydrocolloids, a tackifier, and a plasticizer or solvent. The bandage also includes an intermediate layer of flexible semi-open cell polymeric foam and an outer water impervious flexible polymeric film coating.

SUMMARY OF THE INVENTION

This invention is directed to an improved microporous adhesive tape. The tape includes a porous backing layer and a relatively thick microporous adhesive layer.

DETAILED DESCRIPTION OF THE INVENTION

Figure 1:
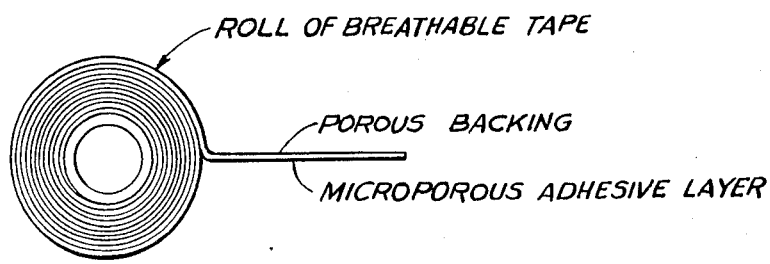
FIG. 1 shows a roll of the microporous adhesive tape of this invention.

As shown in FIG. 1, the breathable adhesive tape of this invention includes a porous backing layer and a microporous adhesive layer. The term microporous is used since the surface of the adhesive layer appears to be continuous but when viewed under a microscope the adhesive layer is revealed to be sponge like having randomly located channels and voids.

The porous backing layer can be formed of woven or non-woven fabric such as the rayon web described by Copeland in U.S. Pat. No. 3,121,021 which is preferred or the porous backing can be an open mesh polymeric substance such as an open mesh polyethylene or polypropylene or a polymeric foam such as polyurethane foam, polyethylene foam or polypropylene foam. The porous backing layer can vary in thickness from about 3 mils to about 20 mils.

The adhesive layer comprises a pressure sensitive rubbery elastomer material having intimately dispersed therein one or more water soluble or water swellable hydrocolloids. Suitable rubbery elastomers include natural or synthetic viscous gum-like substances such as natural rubber, silicone rubber, acrylonitrile rubber, polyurethane rubber, polyisobutylenes, etc., with a mixture of polyisobutylenes of a molecular weight of 5,000 to 11,700 and 81,000 to 99,000 being preferred (these are commercially available as Vistanex and Hyvis). Suitable hydrocolloids include guar gum, sodium carboxymethylcellulose, cross-linked sodium carboxymethylcelulose, pectin, gelatin, alginic acid, locust bean gum, karaya, etc. The viscous gum-like substance acts as a binder for the hydrocolloid particles and, in addition, renders the final adhesive layer tacky, elastic, and pliable.

The hydrocolloid or mixtures of hydrocolloids should comprise from about 20% to 65% by weight of the adhesive layer, preferably from about 30% to about 60% by weight of the adhesive layer. The elastomeric materials should comprise from about 30% to 60% by weight of the adhesive layer, preferably from about 35% to 50% by weight of the adhesive layer.

The adhesive layer can also include up to about 35% by weight of one or more tackifiers, plasticizers or solvents, antioxidants, and preservatives. Suitable tackifiers include terpene resin, which is preferred, a starch-acrylonitrile graft copolymer (such as that commercially available as Poly 35A-100), or a copolymer of polyvinylpyrrolidone and vinylacetate. Suitable plasticizers or solvents include mineral oil, paraffin wax, and petrolatum with mineral oil being preferred. Suitable antioxidants include butylated hydroxytoluene (BHT), which is preferred, and butylated hydroxyanisole (BHA).

The adhesive layer in the final tape varies from about 2 mils to about 10 mils in thickness and contains holes or pores of from about 10 microns to about 300 microns in size and a porosity of about 1 to about 100 cc/sec/in$^2$. The porosity is determined by ASTM D-726-71 method using the Gurley Densometer 4110 at 4.89 inches of water $\Delta P$.

Figure 2:
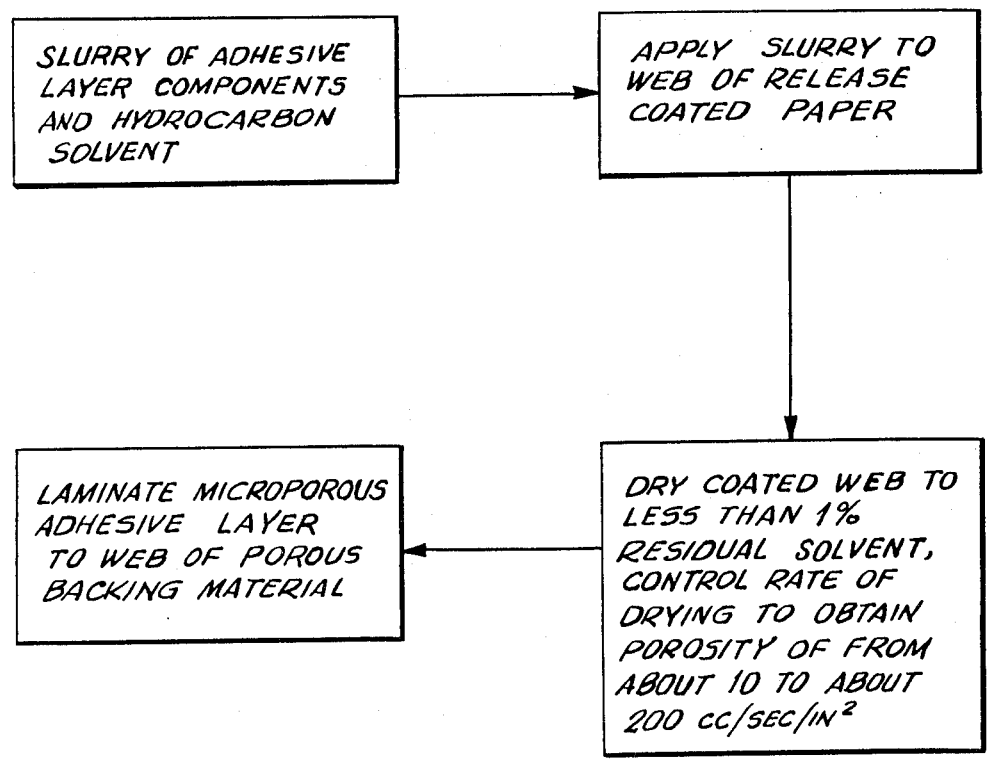
FIG. 2 is a flow sheet of the process by which the microporous adhesive tape is prepared.

The microporous tape of this invention is prepared according to the flow sheet of FIG. 2. The various components of the adhesive layer, i.e., the hydrocolloids, rubbery elastomers, tackifiers, plasticizers, antioxidants and preservatives, are dispersed in a hydrocarbon solvent such as toluene, heptane, or hexane or mixtures thereof to form a slurry. The slurry is then deposited, for example, by means of a knife-over-roller, onto a web of silicone coated release paper. The slurry is deposited at a wet thickness of from about 5 mils to about 40 mils, preferably about 10 mils thick. The release paper having the adhesive layer is then passed through a drying tunnel, for example, a multi-zone hot air oven, where it is dried to less than 1% by weight of residual solvent. The air temperature and velocity through the drying zone are controlled so that numerous small bubbles are generated from the solvent evaporation resulting in voids in the adhesive layer which provide the desired microporosity. The dry adhesive layer is then laminated to a web of porous backing material suitably positioned so that the adhesive layer is pressed into intimate contact with the porous backing material. The silicone coated release paper may be left on the resulting tape or it may be stripped off entirely.

The resulting tape can be wound onto a roll or cut into sheets and packaged in strip form. If the tape is wound onto a roll, the outer surface of the porous backing material should be coated with a release agent. The final tape can be sterilized by irradiation or other techniques.

The breathable microporous tape of this invention can be used for various medical or health care purposes where adhesion to the skin is desired. The tape of this invention permits air to permeate down through the microporous adhesive layer to the skin. The adhesive layer unlike conventional pressure sensitive adhesives does not cause irritation, itch, or excoriation of the skin. The hydrocolloids present in the adhesive layer absorb moisture such as perspiration or wound exudates and transfers such moisture from the surface of the skin to the porous backing material where it can evaporate.

The adhesive layer of the instant tape by regulating the moisture level at the surface of the skin enables the tape to remain firmly in place for long periods of time and reduces or eliminates the need for the tape to be changed.

The following examples are illustrative of the invention.

EXAMPLE 1

A breathable tape is prepared having the following microporous adhesive layer

| Ingredient | Percent by Weight of the Adhesive Layer |
|---|---|
| Sodium carboxymethylcellose | 18% |
| Gelatin (powder) | 15% |
| Polyisobutylene average molecular weight of 81,000–99,000 (Vistanex L-100) | 20% |
| Polyisobutylene average molecular weight of 10,000–11,700 (Vistanex LM-MH) | 18% |
| Terpene resin | 20% |
| Mineral oil | 8.5% |
| Butylated hydroxytoluene | 0.5% |

The above solids are dispersed in sufficient heptane to make a slurry containing 40% by weight solids. The slurry is applied via a knife-over-roller onto silicone coated release paper to a wet thickness of 10 mils. The material is then passed through a multi-zone oven with a residence time of 5–10 minutes so as to reduce the solvent content to less than 1%. The resulting dry adhesive layer is 3 mils thick and has a porosity of about 5 cc/sec/in$^2$. As the dry film emerges from the oven, it is laminated to a web of non-woven porous fabric coming from a roll suitably positioned so that the adhesive is pressed into intimate contact with the non-woven material.

EXAMPLES 2–12

Following the procedure of Example 1 but forming the adhesive slurry of the following ingredients additional microporous tapes within the scope of this invention are obtained.

| Ingredient (% by weight) | 2 | 3 | 4 | 5 | 6 | 7 | 8 | 9 | 10 | 11 | 12 |
|---|---|---|---|---|---|---|---|---|---|---|---|
| Polyisobutylenes | 40% | 45% | 45% | 45% | 40% | 40% | 46% | 38% | 38% | 40% | 40% |
| Guar Gum | 40% | 20% | 35% | 25% | 25% | 25% | — | — | — | — | — |
| Sodium Carboxymethylcellulose | — | — | — | — | 10% | 10% | 18% | 18% | 18% | — | 20% |
| Gelatin | — | — | — | — | — | — | 18% | 15% | 15% | — | 20% |
| Pectin | — | 20% | — | 15% | — | — | 18% | — | — | — | — |
| Alginic acid | 3% | — | — | — | — | — | — | — | — | 3% | — |
| Locust Bean Gum | — | — | — | — | — | — | — | — | — | 40% | — |
| Karaya gum | — | — | — | — | — | — | — | — | — | — | 20% |
| Cross-linked sodium carboxymethylcellulose (Aqualon R) | — | — | 15% | — | 15% | 15% | — | — | — | — | — |
| Starch-acrylonitrile graft copolymer sodium salt (Poly 35A-100) | 12% | 15% | — | 15% | 10% | 10% | — | — | — | — | — |
| Polyvinylpyrrolidone-vinylacetate copolymer | 5% | — | 5% | — | — | — | — | — | — | — | — |
| Terpene resin | — | — | — | — | — | — | — | 20% | 20% | 17% | — |
| Mineral oil | — | — | — | — | — | — | — | 8.5% | 8.5% | — | — |
| Butylated hydroxytoluene | — | — | — | — | — | — | — | 0.5% | 0.5% | — | — |
| Adhesive layer thickness (dry) | 5 mils | 4 mils | 7 mils | 5 mils | 5 mils | 5 mils | 9 mils | 2 mils | 5 mils | 4 mils | 8 mils |

What is claimed is:

1. A breathable tape consisting of a porous backing layer and a microporous adhesive layer; said adhesive layer comprising from about 30% to about 60% by weight of a rubbery elastomer selected from the group consisting of natural rubber, silicone rubber, acrylonitrile rubber, polyurethane rubber, and polyisobutylene, from about 20% to about 65% by weight of one or more water soluble or water swellable hydrocolloids selected from the group consisting of guar gum, sodium carboxymethylcellulose, cross-linked sodium carboxymethylcellulose, pectin, gelatin, alginic acid, locust bean gum and karaya gum, and up to 35% by weight of one or more tackifiers, plasticizers, antioxidants, and preservatives; said adhesive layer being at from about 2 mils to 10 mils in thickness and having a porosity of from about 1 to about 100 cc/sec/in$^2$.

2. A tape of claim 1 wherein said adhesive layer comprises from about 35% to 50% by weight of said rubbery elastomer, from about 30% to about 60% by weight of said hydrocolloid or mixtures of hydrocolloids, and up to 35% by weight of said mixture of tackifiers, plasticizers, antioxidants and preservatives.

3. A tape of claim 2 wherein said porous backing layer is a woven or non-woven fabric, an open mesh polymeric substance, or a polymeric foam.

4. A tape of claim 3 wherein said rubbery elastomer is one or more polyisobutylenes.

5. A tape of claim 4 wherein said hydrocolloid is a mixture of guar gum and alginic acid.

6. A tape of claim 4 wherein said hydrocolloid is a mixture of guar gum and pectin.

7. A tape of claim 4 wherein said hydrocolloid is a mixture of guar gum and crosslinked sodium carboxymethylcellulose.

8. A tape of claim 4 wherein said hydrocolloid is a mixture of guar gum, sodium carboxymethylcellulose, and cross-linked sodium carboxymethylcellulose.

9. A tape of claim 4 wherein said hydrocolloid is a mixture of pectin, gelatin, and sodium carboxymethylcellulose.

10. A tape of claim 4 wherein said hydrocolloid is a mixture of sodium carboxymethylcellulose and gelatin.

11. The tape of claim 10 wherein said porous backing is non-woven fabric and said microporous adhesive layer comprises about 18% by weight of sodium carboxymethylcellulose, about 15% by weight of gelatin, about 38% by weight of polyisobutylenes, about 20% by weight of terpene resin, about 8.5% by weight of mineral oil, and about 0.5% by weight of butylated hydroxytoluene.

12. The tape of claim 4 wherein said adhesive layer is 3 mils and has a porosity of about 5 cc/sec/in$^2$.

* * * * *